US005670347A

United States Patent [19]

Gopal

[11] Patent Number: 5,670,347
[45] Date of Patent: Sep. 23, 1997

[54] PEPTIDE-MEDIATED GENE TRANSFER

[75] Inventor: T. Venkat Gopal, North Potomac, Md.

[73] Assignee: AMBA Biosciences LLC, Gaithersburg, Md.

[21] Appl. No.: 240,514

[22] Filed: May 11, 1994

[51] Int. Cl.$^6$ .............. C12N 15/00; C12N 5/06; C12N 15/63
[52] U.S. Cl. .............. 435/172.1; 435/172.3; 435/240.2; 435/320.1; 935/55
[58] Field of Search .............. 435/172.1, 320.1, 435/240.2, 172.3; 935/55

[56] References Cited

U.S. PATENT DOCUMENTS 5,354,844 10/1994 Beug et al. .............. 530/345

OTHER PUBLICATIONS

Rothstein et al., Blood 65(3): 744–752, 1985.
Lau et al. PNAS 81:414–418, 1984.
Garcia-Bustos et al., "Nuclear Protein Localization", *Biochmica et Biophysica Acta.*, vol. 1071:83–101, (1991).
N. Raikhel, "Nuclear Targeting In Plants", *Plant Physiol.*, vol. 100:1627–1632, (1992).
McNally et al., "Optimizing Electroporation Parameters For A Variety of Human Hematopoietic Cell Lines", *Biotechniques*, vol. 6:882–886, (1988).
Michael et al., "Binding-Incompetent Adenovirus Facilitates Molecular Conjugate-Mediated Gene Transfer By The Receptor-Mediated Endocytosis Pathway", *The Journal of Biological Chemistry*, vol. 268:6866–6869, (1993).
RHIM et al., "Neoplastic Transformation Of Human Keratinocytes By Polybrene-Induced DNA-Mediated Transfer Of An Activated Oncogene", *Oncogene*, vol. 4:1403–1409, (1989).
Chaney et al., "High-Frequency Transfection Of CHO Cells Using Polybrene", *Somatic Cell And Molecular Genetics*, vol. 12:237–244, (1986).
Gilboa et al., "Transfer And Expression of Cloned Genes Using Retroviral Vectors", *Biotechniques*, vol. 4:504–512, (1986).
Stuhlmann et al., "Construction And Properties Of Replication-Competent Murine Retroviral Vectors Encoding Methotrexate Resistance", *Molecular And Cellular Biology*, vol. 9:100–108, (1989).
Miller et al., "Improved Retroviral Vectors For Gene Transfer And Expression", *Biotechniques*, vol. 7:980–988, 1989).
Zwiebel et al., "High-Level Recombinant Gene Expression In Rabbit Endothelial Cells Transduced By Retroviral Vectors", *Science*, vol. 243:220–222, (1989).
Fink et al., "In Vivo Expression of β-Galactosidase In Hippocampal Neurons By HSV-Mediated Gene Transfer", *Human Gene Therapy*, vol. 3:11–19, (1992).
Takai et al., "DNA Transfection Of Mouse Lymphoid Cells By The Combination Of DEAE-Dextran-Mediated DNA Uptake And Osmotic Shock Procedure", *Biochimica et Biophysica Acta*, vol. 1048:105–109, (1990).

Tratschin et al., "Adeno-Associated Virus Vector For High-Frequency Integration, Expression, and Rescue Of Genes In Mammalian Cells", *Molecular And Cellular Biology*, vol. 5:3251–3260, (1985).
Hermonat et al., "Use Of Adeno-Associated Virus As A Mammalian DNA Cloning Vector: Transduction Of Neomycin Resistance Into Mammalian Tissue Culture Cells", *Proc. Natl. Acad. Sci. USA*, vol. 81:6466–6470, (1984).
Miller et al., "Redesign Of Retrovirus Packaging Cell Lines To Avoid Recombination Leading To Helper Virus Production", *Molecular And Cellular Biology*, vol. 6:2895–2902, (1986).
Okada et al., "Introduction of Macromolecules Into Cultured Mammalian Cells By Osmotic Lysis Of Pinocytic Vesicles", *Cell*, vol. 29:33–41, (1982).
Holter et al., "Short Note", *Experimental Cell Research*, vol. 184:546–551, (1989).
Mannino et al., "Liposome Mediated Gene Transfer", *Biotechniques*, vol. 6:682–690, (1988).
Nicholas B. La Thangue, "DRTF1/E2F: An Expanding Family Of Heterodimeric Transcription Factors Implicated In Cell-Cycle Control", *Clonexpress, Inc.*, pp. 108–114, (1994).
Johnson et al., "Expression of Transcription Factor E2F1 Induces Quiescent Cells To Enter S Phase", *Nature*, vol. 365:349–352, (1993).
Morin et al., "Nuclear Localization of the Adenovirus DNA-Binding Protein: Requirement for Two Signals and Complementation During Viral Infection", Molecular & Celluar Biology (1989) pp. 4372–4380.
Jenster et al., "Nuclear Import of the Human Androgen Receptor", Biochemical Journal, vol. 293, (1993), pp. 761–768.
Van Der Krol et al., "The Basic Domain of Plant B-ZIP Proteins Facilitates Imprrot of a Reporter Protein into Plant Nuclei," The Plant Cell, vol. 3, American Society of Plant Physiologists (1991), p. 667–675.
Matheny et al., "The Nuclear Localization Signal of NGFI-A Is Located within the Zinc Finger DNA Binding Domain," Journal of Biological Chemistry, vol. 269, No. 11, (1984) pp. 8176–8181.
Schreiber et al., "The Human Poly(ADP-Ribose) Polymerase Nuclear Localization Signal is a Bipartite Element Functionally Separate Fr. DNA Binding & Catalytic Activity" EMBO Jour., vol. 1, No. 9, (1992) pp. 3263–3269.

Primary Examiner—Douglas W. Robinson
Assistant Examiner—Thanda Wai
Attorney, Agent, or Firm—Foley & Lardner

[57] ABSTRACT

A methodology that allows for highly efficient transfer and stable integration of DNA into both established eukaryotic cell lines and primary cells, including non-dividing cells such as human peripheral blood monocytes and macrophages, entails the use of a synthetic polypeptide comprised of a peptide domain which corresponds to a nuclear localization signal sequence and a DNA binding domain which is rich in basic amino acids, separated by a hinge region of neutral amino acid which prevents stearic interference between the two domains.

14 Claims, No Drawings

PEPTIDE-MEDIATED GENE TRANSFER

BACKGROUND OF THE INVENTION

The present invention is directed to a methodology for highly efficient, stable integration of DNA into a eukaryotic genome. More specifically, the present invention is directed to the use of a synthetic polypeptide, containing a nuclear localization signal, to complex with a DNA molecule and to facilitate its transportation and integration into the nuclear genome of a mammalian or other eukaryotic cell, for example, in the context of producing cell lines with an extended life.

DNA-CaPO$_4$ co-precipitation was the first method developed to introduce genes into mammalian cells. ("Gene" in this regard denotes a structural DNA segment, i.e., a DNA that codes for a polypeptide, and comprehends oncogenes as well as DNAs coding for a known expression product.) The co-precipitation method was applicable only to certain cell types, however, and could not be used to introduce genes into a wide variety of cell lines, especially those of hematopoietic origin. Moreover, the stable gene transfer efficiency was rather low, on the order of $10^{-4}$ to $10^{-6}$. McNally, M. A., et. al., *BioTechniques* 6: 8826 (1988); Yen, T. S. B., et. al., loc. cit. 6: 413 (1988).

Limits on introducing and expressing genes in cultured mammalian cells motivated a search for other, more efficient approaches to gene transfer. Methods were developed, for example, that utilized chemical agents which were positively charged and, hence, able to complex with negatively charged DNA molecules. Examples of such agents include DEAE dextran and various cationic lipid molecules. Cells treated with DNA complexes comprised of such an agent can lead to the introduction of the DNA into different mammalian cell lines. Mannino, R. J. et. al., *BioTechniques* 6: 682 (1988); Felgner, P. et al., *Proc. Nat'l Acad. Sci. USA* 84: 7413 (1987); Fraley, R. et. al., *Trend Biochem. Sci.* 6: 77 (1981); Holter, W. et. al., *Exp. Cell Res.* 184: 546 (1989); McCutchan, J. H. et al., *J. Nat'l Cancer Inst.* 41: 351 (1986); Chaney, W. C. et al., *Somatic Cell & Mol. Genet.* 12: 237 (1986).

The production of a gene product for only a short time period after transfection, usually from 48 to 72 hours, is called "transient expression." Many of the DNA-complexing agents reported heretofore, while useful in transferring a gene into mammalian cells, resulted in only transient expression of the introduced gene in a small fraction of the transfected cells. See, for example, Miller et. al., *Proc. Nat'l Acad. Sci., USA*, 76: 949 (1979); Oi et al., loc. cit. 80: 825 (1983).

In addition to giving poor results with respect to stable gene expression, transfer methods based on such DNA-complexing agents often were effective only with established cell lines, and did not work very well with primary cells isolated from various mammalian species. Other techniques therefore were needed to enhance gene transfer efficiency, to increase the variety of cell types capable of being transfected, and to effect stable gene transfer. Stable gene transfer is the ability of cells to maintain and express transfected DNAs in a stable manner, through integration of the transfected DNA into cell chromosomes.

Retrovital vectors, which were under development at about the same time seemed to be quite effective in transferring genes into different cell types. The use of such vectors was prompted by the elucidation of gene regulation in various murine and avian retroviruses. Two other developments led to the development of retrovirus-based gene transfer vehicles. The first development was the identification of minimal sequences required for efficient packaging of viral particles in a cell line which produced the coat proteins and other structural components of the viral particle in trans. The cell lines that provided the structural components for virus development are called "packaging" cell lines. The second significant step in the establishment of retroviral vectors was the development of both ecotropic and amphotropic packaging cell lines, which aided the design of recombinant retroviral particles which could infect both murine and human cell lines.

Additional modifications of retroviruses were deemed necessary to address concerns that retroviral vectors could recombine in vivo to generate wild-type virus. Developments in this regard yielded a number of safe retroviral vectors which have been used to transfer genes into a variety of established mammalian cell lines, as well as into certain primary cells in a few instances. E. Gilboa et al., *BioTechniques* 4: 504 (1986); A. D. Miller et al., *Mol. Cell. Biol.* 6: 2895 (1986); H. Stuhlmann et al., loc. cit. 9: 100 (1989); A. D. Miller et al., *BioTechniques* 7: 980 (1989); J. A. Zwiebel et al., *Science* 243: 220 (1989).

Even though these vectors were effective with respect to various mammalian cells, there were many restrictions on a wider application of the retroviral gene-transfer technique. These limitations included (1) the size of exogenous DNA that can be inserted into a retroviral vector and (2) the use of only dividing cells for retroviral gene transfer. E. Gilboa, *BioTechniques*, supra (1986); A. D. Miller, supra (1986); H. Stuhlmann, et al., *Mol. Cell. Biol.* supra, (1986); A. D. Miller et al., *BioTechniques, supra* (1986); J. A. Zwiebel et al., supra (1989).

Other viruses have been used to generate recombinant viral vectors for gene transfer studies. Adenovirus, adeno-associated virus, herpes simplex virus, and even HIV have been employed as vectors to introduce genes into both established cell lines and primary cells. Some of these viral vectors are capable of transferring genes into non-dividing cells. R. J. Samulski, et al., EMBO J. 10: 3941 (1981); J. D. Tratschin, et al., *Mol. Cell. Biol.* 5: 3251 (1985); P. L. Hermonat, et al., *Proc. Nat'l Acad. Sci. (USA)* 81: 6466 (1984); D. J. Fink, et al., *Human Gene Therapy* 3: 11 (1992).

Viral vectors capable of transferring genes into non-dividing cells usually require the generation of high-titer viral stock in order to achieve high efficiency gene transfer into different cell types. In addition, whenever a different regulatory sequence is to be tested for optimal level of gene expression into primary cells, a new viral stock must to be made and tittered for every modification. All these involve very time-consuming experimental manipulations.

Still another concern relates to the application of viral vectors in human gene therapy. A number of studies have been carried out in primates to test the safety of retroviral vectors for introducing cells transduced with retroviral vectors into animals. Some of these animals have developed various forms of lymphoma. R. E. Donahue, et al., *J. Exp. Med.* 176: 1125 (1992). Additional safety features have been introduced into some of the newer versions of retroviral vectors, yet are not available for all types of viral vectors.

SUMMARY OF THE INVENTION

It therefore is an object of the present invention to provide a method for high efficiency gene transfer to achieve expression, stable as well as transient, in a wide spectrum of cell types, including primary cells from various mammalian species.

It is also an object of the present invention to provide cell lines which, even if derived from primary mammalian cells, are characterized by an extended life in culture.

It is another object of the present invention to provide a readily implemented screening system for identifying sequences that influence in the expression of cloned genes in various primary cell types from different species.

In accomplishing these and other objectives, there has been provided, in accordance with one aspect of the present invention, a transfection vector comprising a synthetic polypeptide linked electrostatically to a DNA structural sequence, forming a polypeptide-DNA complex, where the polypeptide is comprised of (A) a polymeric chain of basic amino acid residues, (B) an NLS peptide and (C) a hinge region of neutral amino acids that connects the polymeric chain and the NLS peptide. The polymeric chain preferably is comprised of between 10 and 50 residues, which can selected from lysine, arginine and ornithine, for example, while the hinge region is comprised of between 6 and 50 amino acid residues selected, for example, from glycine, alanine, leucine and isoleucine. The NLS peptide preferably is located at the amino terminus of said polypeptide and the polymeric basic amino acid chain at the carboxyl terminus. Among exemplary NLS peptides are the SV40 large T antigen NLS sequence, the polyoma large T antigen NLS sequence, the adenovirus E1a NLS sequence, and the adenovirus E1b NLS sequence.

In accordance with another aspect of the present invention an extended life cell line is provided that is the product of transfecting a mammalian cell with a vector as described above. The mammalian cell thus transfected can be selected, for example, from the group consisting of a human umbilical vein endothelial cell, a human dermal microvascular endothelial cell, a human peripheral blood monocyte/macrophage cell, a human aortic smooth muscle cell, and a rabbit liver non-parenchymal cell.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The present invention allows for the highly efficient transfer and stable integration of DNA into eukaryotic cells, such as cells from established mammalian cell lines, primary cells from mammalian tissues, and plant cells. The present invention also can be applied to developing cell lines from non-dividing cells, such as human peripheral blood monocytes and macrophages.

In accordance with the present invention, a synthetic polypeptide is provided that can complex with a DNA molecule very efficiently by taking advantage of the high negative charge density on the polynucleotide. To this end, a synthetic polypeptide of the present invention comprises a DNA-binding sequence that is rich in basic amino acids, such as lysine, arginine and ornithine, and that is typically ten to fifty residues long. D-isomers of these basic amino acids are suitable so long as the length of the stretch of basic amino acids is within the prescribed length. The DNA-binding sequence can be a homopolymer of a basic amino acid, or it can comprise more than one kind of basic residue. The DNA binding sequence must be of adequate length to bind DNA, yet not so long that it precipitates out of the solutions employed in the present methodology, as discussed below.

A synthetic polypeptide of the present invention also contains an amino acid sequence corresponding to a nuclear localization signal (NLS) sequence. A representative sample from the diverse range of nuclear localization signals which have been identified are listed in Table I below. (SEQ ID NOS:1–54).

TABLE 1

| Source | Nuclear Protein | Deduced Signal Sequence |
|---|---|---|
| Yeast | MATα2 | (SEQ ID NO: 1) K—I—P—I—K |
| | | (SEQ ID NO: 2) V—R—I—L—E—S—W—F—A—K—N—I |
| SV40 | Large T | (SEQ ID NO: 3) P—K—K—K—R—K—V |
| Influenza virus | Nucleoprotein | (SEQ ID NO: 4) A—A—F—E—D—L—R—V—R—S |
| Yeast | Ribosomal protein L3 | (SEQ ID NO: 5) P—R—K—R |
| Polyoma virus | Large T | (SEQ ID NO: 6) V—S—R—K—R—P—R—P—A |
| SV40 | VP1 | (SEQ ID NO: 7) A—P—T—K—R—K |
| Adenovirus | E1a | (SEQ ID NO: 8) K—R—P—R—P |
| SV40 | VP2 (VP3) | (SEQ ID NO: 9) P—N—K—K—K—R—K |
| Frog | Nucleoplasmin | (SEQ ID NO: 10) R—P—A—A—T—K—K—A—G—Q—A—K—K—K—K—L—D— |
| Rat | Glucocorticoid receptor | (SEQ ID NO: 11) K—K—K—I—K |
| Monkey | v-sis (PDGF B) | (SEQ ID NO: 12) R—V—T—I—R—T—V—R—V—R—R—P—P—K—G—K—H—R—K |
| Yeast | Histone 2B | (SEQ ID NO: 13) G—K—K—R—S—K—A |
| Chicken | v-rel | (SEQ ID NO: 14) K—A—K—R—S—K—A |
| Influenza | NS1 | (SEQ ID NO: 15) D—R—L—R—R |
| | | (SEQ ID NO: 16) P—K—Q—K—R—K |
| Frog | N1 | (SEQ ID NO: 17) V—R—K—K—R—K—T |
| | | (SEQ ID NO: 18) A—K—K—S—K—Q—E |
| Human | c-myc | (SEQ ID NO: 19) P—A—A—K—R—V—K—L—D |
| | | (SEQ ID NO: 20) R—Q—R—R—N—E—L—K4-S—F |
| Human | lamin A | (SEQ ID NO: 21) T—K—K—R—K—L—E |
| HTLV-1 | Rex(p27$^{x-III}$) | (SEQ ID NO: 22) P—K—T—R—R—R—P |
| | | (SEQ ID NO: 23) S—Q—R—K—R—P—P |
| Adenovirus | $_F$TP | (SEQ ID NO: 24) R—L—P—V—R—R—R—R—R—V—P |
| HIV-1 | Tat | (SEQ ID NO: 25) G—R—K—K—R |
| Frog | Lamin L$_1$ | (SEQ ID NO: 26) V—R—T—T—K—G—K—R—K—R—I—D—V |

TABLE 1-continued

| | | |
|---|---|---|
| Rabbit | Progesterone receptor | (SEQ ID NO: 27) R—K—F—K—K |
| HIV-1 | Rev | (SEQ ID NO: 28) R—R—N—R—R—R—R—W |
| Human | PDGF A-chain | (SEQ ID NO: 29) P—R-3-S—G—K—K—R—K—R—K—R—L—K—P—T |
| Mouse | c-abl | (SEQ ID NO: 30) K—K—K—K—K |
| Adenovirus | DBP | (SEQ ID NO: 31) P—P—K—K—R |
| | | (SEQ ID NO: 32) P—K—K—K—K—K |
| Chicken | c-erb-A | (SEQ ID NO: 33) S—K—R—V—A—K—R—K—L |
| Human | c-myb | (SEQ ID NO: 34) P—L—L—K—K—I—I—Q |
| Human | N-myc | (SEQ ID NO: 35) P—P—Q—K—K—I—K—S |
| Human | p53 | (SEQ ID NO: 36) P—Q—P—K—K—K—P |
| Human | Hsp 70 | (SEQ ID NO: 37) F—K—R—K—H—K—K—D—I—S—Q—N—K—R—A—V—R—R |
| Hepatitis B virus | Core protein | (SEQ ID NO: 38) S—K—C—L—G—W—L—W—G |
| Chicken | Ets1 | (SEQ ID NO: 39) G—K—R—K—N—K—P—K |
| Yeast | Ribosomal protein L29 | (SEQ ID NO: 40) K—T—R—K—H—R—G |
| | | (SEQ ID NO: 41) K—H—R—K—H—P—G |

| Protein | Nuclear Localization Signals |
|---|---|
| TGA-1A (tobacco) | (SEQ ID NO: 42) 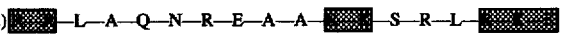—L—A—Q—N—R—E—A—A—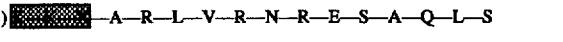—S—R—L— |
| TGA-1B (tobacco) | (SEQ ID NO: 43) 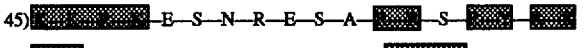—A—R—L—V—R—N—R—E—S—A—Q—L—S |
| | (SEQ ID NO: 44) 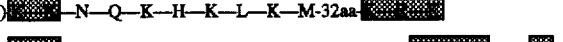—Q—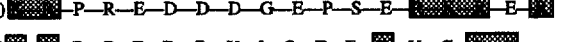 |
| O2 NLS B (maize) | (SEQ ID NO: 45) 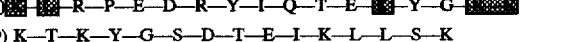—E—S—N—R—E—S—A——S—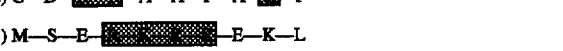— |
| NIa (Polyvirus) | (SEQ ID NO: 46) —N—Q—K—H—K—L—K—M-32aa- |
| VirD2 (Agrobacterium) | (SEQ ID NO: 47) —P—R—E—D—D—D—G—E—P—S—E——E— |
| VirE2 NSE1 (Agrobacterium) | (SEQ ID NO: 48) —R—P—E—D—R—Y—I—Q—T—E——Y—G— |
| VirE2 NSE2 (Agrobacterium) | (SEQ ID NO: 49) K—T—K—Y—G—S—D—T—E—I—K—L—L—S—K |
| O2 NLS A (maize) | (SEQ ID NO: 50) M—E—E—A—V—T—M—A—P—A—A—V—S—S—A—V—V—G—D—P |
| | (SEQ ID NO: 51) M-3-Y—N—A—I—L——L—E—E—D—L—E |
| R NLS A (maize) | (SEQ ID NO: 52) G—D——A—A—P—A——P |
| R NLS M (maize) | (SEQ ID NO: 53) M—S—E——E—K—L |
| RNLS C (maize) | (SEQ ID NO: 54) M—I—S—E—A—L——A-1-G— |

See Garcia-Bustos et al., *Biochem. Biophys. Acta* 1071: 83 (1991), Raikhel, N., *Plant Physiol.* 100: 1627 (1992), and Citovsky, V. et al., *Science* 256: 1802 (1992), the contents of each of which are hereby incorporated by reference.

In the present invention, an NLS peptide, which typically is six to fifteen amino acids in length, facilitates transport of the associated DNA into the nucleus. Because the synthetic polypeptide promotes the transport of the transfected gene into the nucleus of the host cell, this method provides both highly efficient stable and transient gene expression. Once inside the nucleus, the introduced DNA is immediately available to the transcription machinery, and can be expressed transiently. Simultaneously, the introduced DNA is also in the process of getting integrated into the host chromosome to give rise to stable expression. Thus, the method of the instant invention can achieve both transient and stable expression of introduced DNA.

Transient gene expression results when the method of gene transfer results in the introduction of the DNA sequences into the nucleus in an non-integrated form. Transient transfection is measured 24 to 72 hours after transfection by assays that measure gene expression of the transfected gene(s). In contrast, stable expression of the encoded protein results when the transferred DNA sequences are stably integrated into the chromosomal DNA of the target cell. Stable transfectants remain capable of expressing the transfected DNA after two weeks or greater following the method of the invention. Commonly used assays monitor enzyme activities of chloramphenicol acetyltransferase (CAT), LAC-Z, β-galactosidase (β-gal), β-glucuronidase (GUS), luciferase, or human growth hormone, each of which may be contained in the present invention.

The NLS domain of the synthetic peptide is based on known endogenous peptide sequences that were identified by reference to two criteria: (1) sufficient to redirect a cytoplasmic protein to the nucleus and (2) necessary for directing a nuclear protein to the nucleus. Methods for assessing an NLS peptide's ability to direct protein to the nucleus are known in the art. See Garcia-Bustos, et al., supra, Sandler et al., *J. Cell Biol.* 109: 2665 (1989), and Citovsky et al., supra, the respective contents of which are hereby incorporated by reference. For example, an NLS peptide or a natural protein containing an NLS is fused to an otherwise non-nuclear protein, by either synthetic or recombinant production. The hybrid protein is then assessed for its ability to target the non-nuclear protein to the nucleus.

The presence of the non-nuclear protein in the nucleus can be determined by a functional assay or immunofluorescence. An illustrative assay entails the histochemical determination of a product produced by the non-nuclear protein, such as a colorimetric marker produced by β-gal or GUS. (A "colorimetric marker" includes an enzyme that can catalyze a reaction with a substrate to elicit a colored product which can be detected or measured by a variety of means, such as standard fluorescence microscopy, flow cytometry, spectrophotometry or colorimetry. "Immunofluorescence" relates to detecting the presence of the non-nuclear protein in the nucleus by means of an antibody specific for the targeted protein.)

In the past NLS peptides have been studied to assess their ability to target reporter proteins to the nucleus. Also, endogenous proteins containing an NLS, such as the VirD2 and VirE2 of Agrobacterium, have been shown to mediate the transfer of the Agrobacterium single-stranded DNA intermediate T-strand to the plant cell nucleus endogenously. See Citovsky, et al., supra. There has been no suggestion heretofore, however, to use an NLS peptide to target a polynucleotide to the nucleus of a eukaryotic cell.

A preferred NLS domain contains a short stretch of basic amino acids like the NLS of the SV40 virus large T antigen (PKKKRKV) (SEQ ID NO:3), which is an NLS that has been shown to be effective in mammalian cells (basic residues are highlighted). Another preferred NLS domain consists essentially of short hydrophobic regions that contain one or more basic amino acids (KIPIK) (SEQ ID NO:1), which is like the NLS of mating type α2. The NLSs that transport DNA into the plant cell nucleus often are bipartite, which means that they are usually comprised of a combination of two regions of basic amino acids separated by a spacer of more than four residues (see stippled segments in Table I), such as the Xenopus nucleoplasmin (KRPAATKKAGQAKKKK) (SEQ ID NO:55).

The NLS peptide of the present invention can be designed to accommodate different host cells, both mammalian and plant cell hosts.

The method described here can suitably be modified to introduce genes into plant protoplasts using plant NLSs, such as those described by Raikhel (1989), supra.

The present gene transfer system is also capable of transferring foreign DNA into gymnosperms and angiosperms. Procedures for assessing the introduction of foreign DNA in plants are known to the art, such as those disclosed by Miki, B. L., et al., in METHODS IN PLANT MOLECULAR BIOLOGY AND BIOTECHNOLOGY, B. R. Glick et al., eds. (CRC Press, 1993), and Gruber, M. Y. et al., id.

A synthetic polypeptide of the present invention thus is comprised of a DNA binding domain and an NLS peptide domain which are separated by a third element, a hinge region of neutral amino acid, to minimize stearic interference between the two domains. For this purpose, the hinge region ranges in length from about six to twenty-five amino acids, and contains a stretch of neutral small amino acids without any bulky hydrophobic or ionic side chains.

The NLS sequence can be located at either the amino terminus or the carboy-terminus of the synthetic peptide. The arrangement of the two domains, basic amino acid sequence and NLS sequence can be interchanged without affecting the high gene transfer efficiency. As indicated previously, such a synthetic polypeptide binds electrostatically to the DNA that is to be introduced into the target cell. The weight ratio of polypeptide to DNA in the resulting complex generally is in the range of 1:1 to 1:10; for example, 1 μg polypeptide to 1 to 10 μg of polynucleotide.

In accordance with the present invention, entry of the DNA-polypeptide complex into cells can be promoted by treating target cells with a hypertonic solution, followed by hypotonic treatment of cells in the presence of gene-peptide complex. See, for example, Okada and Rechsteiner, Cell 29: 33 (1982). A suitable hypertonic solution can contain both polyethylene glycol (PEG) and sucrose, preferably in the concentration of 0.3M–0.6M and 10% to 25%, respectively, and is referred to as "primer" hereinafter. Okada et al., supra, and T. Takai, et al., Biochem. Biophys. Acta 1048: 105 (1990).

The methodology of the present invention has been used to develop stable transfectants of different established cell lines. It also has been employed to transfer genes into primary cells from different mammalian species, thereby to obtain cell lines that retain many of the characteristics of the cognate primary cells. Cell lines developed from primary cells via the methodology of the present invention are called "extended life" cell lines in this description, because the cell lines so developed retain almost all of the characteristics of their cognate primary cells even in their late passage. The range of cell types that can be converted to extended life cell lines, according to the present invention, is based on the availability of primary cells or the ability to isolate a primary cell from the organ in question. In this regard, the inventive methodology is not limited to cell types amenable to transformation. In addition to the cell types already mentioned, the present invention can be applied to pancreatic beta cells, human liver and kidney cells, and human hematopoietic stem cells, among others.

The methodology of the present invention has been used to develop an extended life cell line from human monocyte/macrophage cells, which are normally non-dividing. In all these instances, stable cell lines were obtained with a very high efficiency, either comparable to or better than the efficiency using retroviral vectors.

The present invention finds application as well in both ex vivo and in vivo gene therapies, where genetic material is transferred into specific cells of a patient. Ex vivo gene therapy entails the removal of the relevant target cells from the body, transduction of the cells in vitro, and subsequent reintroduction of the modified cells into the patient.

A gene therapy pursuant to the present invention could involve an ex vivo introduction, into a particular cell type from the patient, of a polynucleotide coding for a correcting protein which can be produced in functional form by the targeted cell type. Genes suitable for expression in this regard include an adenosine deaminase gene, a globin gene, an LDL receptor gene, and a glucose cerebrosidase gene.

Different kinds of gene-therapy applications require either stable or transient gene expression. The method of the present invention is advantageous in that it can be used in gene therapy requiring either stable gene expression or transient gene expression. Transient expression of a foreign gene is preferred when expression of the exogenous product is needed only for a short period of time; thereafter, rapid clearance of the gene product and its vector is desirable. Transient expression is also desirable when the prolonged effects of the exogenous protein's expression are unknown. Stable expression in gene therapy is needed when the patient has a genetic defect that is incompatible with life. Such genetic defects include but are not limited to cystic fibrosis, Tay Sachs and cancer. Mulligan, Science 260: 926 (1993).

A gene therapy pursuant to the present invention also could involve an in vivo introduction of a structural DNA into cells of a patient's body. For stable transfer of genes into a target tissue using this method, the ligand to the target receptor will be conjugated to the synthetic polypeptide. The polypeptide-ligand combination can be complexed to a polynucleotide coding for the needed protein and then introduced into the host organism through blood circulation. When this complex reaches the target tissue, the whole complex will be taken up by cells containing the corresponding receptor for the ligand through receptor mediated process. Because of the NLS in the polypeptide-ligand complex, the complex will enter into the nucleus, resulting in a stable integration of the introduced gene into the host chromosome and, thereby, a correction of the genetic defect in the host. Cell-specific receptors are well known to those of skill in the art, as are their ligands which can be used in complexes for receptor-mediated gene transfer. Michael, S.

L, et al., *J. Biol. Chem.* 268: 6866 (1993). For example, when the liver is the tissue targeted for gene therapy, the DNA encoding corrective protein is complexed to a synthetic neoglycoprotein that will target the complex to the asialoglycoprotein receptor on hepatocytes. For example, a cell type specific receptor such as asialoglycoprotein can be chemically linked to the transfection vector at the carboxyl terminal of the synthetic polypeptide molecule to deliver the foreign gene directly into liver cells. An additional hinge region can be incorporated into the molecule before chemically linking the polypeptide molecule to a cell-type specific ligand molecule, such as asialoglycoprotein or a cell-specific monoclonal antibody.

An example of a carrier useful for receptor-mediated gene transfer to liver is a synthetic glycoprotein in which bovine serum albumin (BSA) is covalently bound to poly L-lysine using 1-ethyl-3-(3-dimethylaminopropyl) carbodiimide (EDC). Ferkol et al., *FASEB* 7: 1081 (1993). To produce a neoglycoprotein conjugate for use in targeting DNA to liver, a reaction mixture that contains about 170 mM galactose, 4 mM poly (L-lysine), 160 mM BSA and 10 mM EDC (pH 7.5) can be incubated for 48 hours at 22° C. DNA is complexed to the neoglycoprotein carrier in a 360:1 molar ratio. The carrier-DNA complexes are dialyzed against 150 mM sodium chloride before transfection.

Expression of a functional protein after transfection with DNA complexed to ligand alone is often transient. Ferkol et al., supra. The method of the present invention greatly improves the cell-specific targeting of receptor-mediated transfection by providing stable expression by increasing stable integration of a foreign DNA in the host cell using a synthetic polypeptide molecule of the present invention.

A variation of receptor-mediated gene transfer employs coupling a synthetic polypeptide as described above to monoclonal antibodies which recognize a cell surface antigen on the target cells. Maruyama et al., *Proc. Nat'l Acad. Sci. USA* 87: 5744 (1990). The coupled monoclonal antibody and synthetic polypeptide then are complexed with a DNA encoding the required or desired protein. This complex will target the DNA to the cells expressing the corresponding cell surface antigen. Any tissue of the human body can be targeted for the gene therapy of the present invention using the disclosed methods. A target tissue is suitable in this context so long as it is susceptible to genetic modification according to the present invention.

The present invention is further described with reference to the following examples, which are only illustrative and not limiting of the invention.

EXAMPLE 1

Transfer of Genes into Established Cell Lines for Purposes Transient Gene Expression and Selection of Stable Transfectants, Respectively Forming the DNA-Polypeptide Complex and Transfecting Cells Therewith The DNA or other polynucleotide to be transfected, such as a plasmid containing a gene for a drug resistance marker or coding a protein needed for expression in the host cell, is complexed to a synthetic polypeptide molecule in different weight ratios in an isotonic buffer solution. For example the weight ratio of DNA:polypeptide can be between 1:1 and 10:1, although ratios outside of this range may be evaluated empirically for achieving the objects of the present invention. An isotonic buffer solution such as Hanks buffered salt solution or HEPES buffered saline may be used for complexing DNA to polypeptide.

While the complex is formed, the cells that are to be transfected either remain attached to a substratum, such as a tissue culture dish, or are pelleted (for cells that grow in suspension). The cells are treated with a hypertonic primer solution, such as a concentration of 0.3M–0.6M sucrose and 10% PEG in either Tris-HCl or HEPES (pH 7.2) buffered solution, for 3–5 mins at room temperature. The primer solution then is removed.

After the DNA-polypeptide complex is formed, it is made hypotonic. The complex solution is hypotonic when it has a lesser osmotic pressure than a 0.15M or 0.9% solution of NaCl. For example, the complex in isotonic buffer can be made 40–55% hypotonic or 0.075M simply by adding an amount of distilled water that is equal to the volume of the complex in isotonic buffer. The hypotonic complex solution then is added to the cells that have been treated with the primer solution. Cells remain in the hypotonic DNA-polypeptide solution for 3–4 minutes. Fresh medium then is added to the cells to rinse away excess DNA-polypeptide solution. Thereafter, the cells are grown normally.

Producing a Synthetic Polypeptide Molecule

An example of an synthetic polypeptide molecule of the present invention is one consisting of the amino acid sequence PKKKRKVSGGGGGKKKKKKKKKKKK(SEQ ID NO:56). Such a peptide can be synthesized, using standard methods of peptide production, and purified by standard methods using high pressure liquid chromatography (HPLC).

Selection of Stably Transfected Cell Lines

Transfected cells are grown in regular growth medium for 48 hours, and then plated in selective medium containing 400 µg/ml of G418. Cells were plated at a density of 100–1000 cells per 60 cm$^2$ dish. The number of G418-resistant colonies was determined two weeks after the initiation of selection. Other selectable markers, such as pHyg, may be used to achieve the results of the instant invention. K. Blochlinger, et al., *Mol. Cell. Biol.* 4: 2929 (1984).

This method gave a stable-transfection efficiency of 5–10%. Similar results were obtained using either G418 or hygromycin selection. In general the stable transfection efficiency achieved by the method of the instant invention is a few orders of magnitude greater than prior art methods. The instant invention's 5–10% efficiency is several orders of magnitude better than the efficiency of the DNA-CaPO$_4$ co-precipitation method and at least equal or 5 times greater than the fairly high 1–10% level of stable transfection efficiency achieved by viral based methods.

TABLE II

| Method | Stable Transfection Efficiency |
|---|---|
| Peptide-Mediated Gene Transfer | 5–10% |
| Retroviral vectors | 1–10% |
| Non-viral methods (e.g., CaPO$_4$) | <2% |

That the transfectants of the instant invention are stable is shown by the following example. When G418 resistant colonies were grown without selection for variable period of times, and then tested for resistance to the antibiotic by plating the cells under clonal conditions, the same number of colonies were obtained both with and without G418. This result indicates that, once the cells are selected for the expression of the Neo gene, the resistance gene was retained stably in the chromosome.

Three different cell lines were used to test the efficiency of gene transfer of the new method. Mouse fibroblast cell line (L cells), mouse erythroleukemia cell line (C19TK), and COS cells. The COS cell line was used to establish conditions for transient gene expression. The eukaryotic expression vector, CH110, contains bacterial β-gal and was employed in these studies. The β-gal gene in CH110 is under the control of SV40 virus early promoter.

The COS cells were treated with primer and then exposed to DNA-polypeptide (2.5–5.0 µg) complex under hypotonic conditions. After this treatment, cells were returned to the normal growth condition. Transfected cells were grown at 37° C. for 48 hrs, and stained for the expression of the β-gal reporter gene. Forty to fifty percent of the cells were positive for the expression of the reporter gene.

Mouse L cells were transfected with eukaryotic expression vector containing the Neo gene, which codes for the antibiotic G418 resistance gene. L cells are sensitive to G418 at 400 µg/ml. Cells plated in 24-well tissue culture plates were then transfected with synthetic polypeptide complexed to the plasmid pRSV-Neo via the methodology of the present invention.

A mouse erythroleukemia cell line, C19TK, also was used as a representative cell line for testing the transfection efficiency of the present invention with respect to hematopoietic cells. The expression vector, pDR2, which carries a hygromycin-resistance gene, was used for these studies. C19TK cells are exquisitely sensitive for the antibiotic hygromycin. This cell line grows in suspension and, hence, was transfected in suspension.

Briefly, about million cells are spun down and the cell pellet is treated with primer. The cells are then exposed to DNA-polypeptide complex under hypotonic condition. Forty-eight hours after transfection, a known number of cells are plated in microtiter plates with hygromycin. The number of wells with growing population of cells was enumerated to determine the transfection efficiency. The stable transfection efficiency was about 1–5%, as compared to most of the other non-virus-based methods that are very poor. Thus, the method described herein is very efficient for stable transfection efficiency both for hematopoietic and non hematopoietic cell lines. Only some retrovirus based vectors give a transfection efficiency comparable to the efficiency obtained with the current method for hematopoietic cell lines. See Gilboa, et al. (1986), Miller, et al. (1986), Stuhlmann, et al. (1989), Miller, et al. (1989), and Zwiebel, et al. (1989), each cited above.

EXAMPLE 2

Transfer of Genes into Human Primary Cells

The gene transfer method of the present invention was used to generate extended life cell lines from different human primary cells. Most of the primary cells have a limited in vitro life span. The following cell types were employed to test the efficacy of the inventive method to generate extended-life cell lines by transfer of various oncogenes, either singly, in pairs of combinations, or combinations of more than two oncogenes. Rhim, J. S., et al., *Oncogene* 4: 1403 (1989).

EXAMPLE 3

Production of Extended Life Cell Lines

The method of introducing genes into primary cells is the same as that described above for introducing genes into established cell lines, such as the mouse fibroblast cell line L cells and the mouse erythroleukemia cell line C19TK. The main difference is that the host cell is a primary cell isolated from different species, human or other mammalian species, and the primary cells have only a limited in vitro life span. The isolation of primary cells from various tissue sources are well known to those of skill in the art.

In order to extend the life of primary cells that are endogenously incapable of extended growth in vitro, the cells are transfected with different oncogenes, such as SV40 large T antigen, polyoma large T antigen, adenovirus E1A and E1B, v-fms, Bcl2, myc and ras. The oncogenes can be used either alone, in pairs of various combinations, or in combinations of more than two oncogenes.

In addition, other genes that do not come under the category of oncogenes may be used. For example, genes that are important for DNA synthesis and normally active during the S phase of the cell cycle, such as the dihydrofolate reductase gene (DHFR), thymidine kinase gene, thymidylate synthetase gene, a DRTF1/E2F transcription factor encoding DNA, or DNA encoding the E2F transcription factor can be complexed to synthetic polypeptide and used to extend the life of primary cells. The human DHFR gene complexed to synthetic polypeptide can be introduced into primary cells to produce extended life cell lines. DNA encoding a transcription factor that is active during the S phase of the cell cycle are particularly useful in the method of the instant invention. La Thangue, N. B. *Trends in Biochemical Sciences* 19: 108 (1994); Johnson, D. G. et al., *Nature* 365: 349 (1993), the respective contents of which are hereby incorporated by reference.

Because untreated primary cells have only a limited life span in vitro, their ability to grow continuously in culture after treatment with the present invention served to select for extended life cell lines. No other drug selection markers need to be used to select for extended life cell lines derived from primary cells.

To produce extended life cells lines from primary cells, newly cultured primary cells were treated by the method of the present invention employing synthetic polypeptide conjugated with various oncogenes, such as SV40 large T antigen and/or Adeno E1A. The treated cells were plated in their appropriate growth media and passed after the cells reached confluency. A parallel set of a control untreated primary cells were cultured under the same growth conditions. Typically, control primary cells stop growing after about 4–10 passages, depending upon the cell type (cell split ratio was usually 1:4 by surface area). In contrast, continuously growing cell lines were obtained from different primary cell types described in the following examples.

EXAMPLE 4

Analysis of Transformed (Extended Life) Cells

Extended life cell lines containing the oncogene are identified by restriction cleavage, Southern analysis and/or Northern analysis using appropriate DNA probes.

The DNA of each transformed extended life cell line is analyzed by Southern hybridization to determine whether the cell lines carry the oncogenes used to establish such extended life cell lines. DNA is extracted from the cell lines and the nucleic acid pellet is re-suspended in 200 µl of 10 mM Tris-Cl pH 7.4, 0.1 mM EDTA, and 10 µg is digested with a specific restriction enzyme, electrophoresed through 1.0% agarose, and transferred to nitrocellulose. Southern, *J. Mol. Biol.* 98: 503 (1975). Filters are hybridized to a radioactively labelled DNA, encoding each of the oncogenes, that gave rise to the corresponding extended life cell line, in the presence of 10% dextran sulfate. After overnight hybridization, the filters were washed twice in 2 X SSC, 0.1% SDS at 64° C.

Each transformed extended life cell line is analyzed by Northern hybridization to determine whether the cell lines transcribe the oncogenes. Cells not containing the oncogene of interest will not demonstrate transcripts in a Northern analysis whereas cells containing the DNA of interest will demonstrate a detectable transcript. Also, an ELISA method was used to detect the presence of oncogene products in some of the extended life cell lines, using publicly available antibodies that recognize the corresponding oncogene protein.

The presence of SV40 large T antigen and adenovirus E1A gene products in the HUVEC extended life cell line, as detected by ELISA, are shown in table 2. Briefly, the cell line grown in a 96 well tissue culture plate is fixed with glutaraldehyde and paraformaldehyde. The cells are then treated with antibodies to the corresponding oncogenes. Thereafter, the cells are washed and then treated with a secondary antibody linked with to β-galactosidase. The cells are washed and then treated with a substrate for β-galactosidase. The reaction develops a product which is then measured using a microplate reader.

To determine whether the extended life cell line has maintained the parental cell line phenotype may be determined by a number of ways. Extended life cells lines containing the oncogene are assessed by Northern analysis using a DNA probes encoding a cell-specific protein. The cell-specific DNA probe is labeled with $^{32}$P-dCTP by nick translation pursuant, for example, to Rigby et al., *J. Mol. Biol.* 113: 237 (1977). Northern hybridization indicates that the extended life cell line is capable of transcribing the cell-specific protein.

Also, the maintenance of the parental phenotype in cells lines established according to the present invention can be determined by a number of biochemical methods, such as ELISA and enzyme assays, that determine the presence or function of a protein specific to the parental cell line. An antibody recognizing a protein produced only by the parental cell line can be used in an ELISA or immunofluorescence assay. Cell-specific markers are well known to those of skill in the art. For example, albumin is a marker for hepatocytes, insulin is a marker for pancreatic beta islet cells, factor VIII is a marker for endothelial cells, actin and myosin are markers for smooth muscle cells, and non-specific esterass is a marker for brain microglial cells. In Table II, the parental phenotype of the extended life endothelial cells produced by the present method of the invention was verified by several ELISAs to determine the expression of cell-specific endothelial markers. The parental phenotype of the monocyte/macrophage extended life cell lines produced by the present method was verified using a lysozyme enzyme assay to measure macrophage specific markers.

EXAMPLE 5

Human Umbilical Vein Endothelial Cells

Endothelial cells isolated from the human umbilical vein can only be cultured for a limited of passages, usually five to six. These cells were transfected with a combination of oncogenes, SV40 large T antigen and adenovirus E1A, or with another combination of genes. At least two oncogenes are needed to develop a truly transformed cell line. Ruley, H. E., et al., *Nature* 304: 602 (1983). For the instant invention, SV40 large T antigen combined with v-myc or ras or some an other oncogene can be used. When the gens encoding SV40 large T antigen is combined with either adenovirus E1A or E1B genes in the method of the instant invention, extended life cell lines may be produced from human umbilical vein endothelial cells. E1A or E1B or SV40 large T antigen alone did not give rise to established cell line with the high frequency obtained from using SV40 large T antigen in combination with E1A or E1B. Synthetic polypeptide complexed to DNA encoding either the SV40 large T antigen or polyoma large T antigen combined with the E2F1 transcription factor gens also produces extended life HUVEC cells lines.

Since the non-transfected primary cells normally grow in vitro only for a limited population doublings, cells that have taken up the oncogenes capable of generating extended life span cell lines were selected simply by repeated passage of the cells. When the transfected population of cells grows continuously, as compared to a control population of parental cells, it is reasonable to conclude that the oncogenes used are capable of generating extended life cells from a given cell type.

In HUVEC, for example, SV40 large T antigen and adenovirus E1A or E1B were effective in giving rise to a cell line. This cell line has now been growing in culture for 40 passages. In contrast, normal HUVECs stop growing by passage 7 or 8. Such cell lines arose with a high efficiency. It also is possible to generate cell lines using as few as a couple of hundred cells, grown either in a 24- or 48-well plate. These cells also have the same morphological appearance as the primary HUVEC and also display many of the biochemical properties characteristic of normal HUVEC.

Some of the properties that are characteristic of endothelial cells that were measured in the HUVEC extended life cell line are also listed in Table 2. These properties were also measured by ELISA using specific antibodies listed in the Table 2.

TABLE III

ELISA assay for the expression of ELAM-1, VCAM-1, ICAM-1, SV40 large T antigen and adenovirus E1A by extended life HUVEC line

| Antibody | O.D.$_{570}$ | |
|---|---|---|
| | −IL-1 | +IL-1 |
| Control | 0.071 | 0.069 |
| Anti ELAM-1 | 0.212 | 1.016 |
| Anti VCAM-1 | 0.146 | 0.520 |
| Anti ICAM-1 | 0.422 | 1.524 |
| Anti SV40 large T | 0.618 | — |
| Anti E1A | 0.725 | — |

EXAMPLE 6

Human Cord Blood-Derived Monocyte Cell Line

Adherent cells from human cord blood cells were transfected with different combinations of oncogenes in suspension using the method of the present invention. The resulting cells are selected in Granulocyte-Macrophage Colony Stimulating Factor (G-CSF). Control cells did not grow in culture, whereas growing populations of monocytes were obtained with several combinations of oncogenes. One preferred combination of polyoma large T antigen and adenovirus E1B encoding DNA produced extended life monocyte cells lines with somewhat higher efficiency than other combinations. Another preferred combination of SV40 large T or polyoma large T antigen and the E2F1 transcription factor gene produces monocyte extended life cells with high efficiency. The monocyte extended life cells also display many of the properties of normal monocytes, which illustrates the utility of the present invention in generating cell lines of hematopoietic origin.

EXAMPLE 7

Extended Life Human Aortic Smooth Muscle Cells

The method of the instant invention has also been used to generate extended life cell lines using a specific combination of oncogenes. Human aortic smooth muscle cells were obtained from Clonetics Corporation (San Diego, Calif. U.S.A.) and transfected with several combination of oncogenes. The combination of polyoma large T antigen and EiB gave rise to a continuously growing population of smooth muscle cells. Another preferred combination of SV40 large T or polyoma large T antigen and the E2F1 transcription factor gene produces extended life human aortic smooth muscle cells with high efficiency. This cell line resembles the early passage primary aortic smooth muscle cells morphologically. The extended life human aortic smooth muscle cells also express smooth cell actin and myosin well beyond passage 20.

EXAMPLE 8

Other Extended Life Cell Types

Primary cells from other species, such as rabbit and monkey, also have been used to generate cell lines. Transfection methods employed for primary cells from non-human species are similar to those used for human primary cells. When developing an extended life cell line from a new primary cell, several different combinations of available oncogenes should be tried. For example, at least five or six pairs of combinations of SV40 large T antigen, adenovirus E1A, adenovirus E1B, polyoma virus large T antigen or others available to those in the art. That combination of genes that gives rise to an extended life cell lines from a given primary cell type is determined as described in the above examples.

When the E2F1 transcription factor gens is complexed to synthetic polypeptide in combination with DNA encoding either the SV40 large T antigen or polyoma large T antigen, extended life cells lines can be produced from a variety of primary cell types, such as HUVEC, dermal microvascular endothelial cells, human aortic smooth muscle cells, and bone marrow monocyte/macrophage cells. Thus, the method of the present invention can identify a combination of oncogene DNAs that is highly efficient in producing extended life cells lines from the primary cells of various species. The present invention also comprehends a combination of an oncogene and an S-phase transcription factor gens which likewise is highly efficient in producing extended life cells lines from different types of primary cells.

EXAMPLE 9

Identification of Cell Type-Specific Transcriptional and Translational Regulatory Sequences The present invention provides a screening system for identifying sequences that influence the expression of cloned genes in various primary cell types from different species. The instant invention can identify cell type specific transcription and translational regulatory sequences. The sequence in question typically will be cloned into a vector containing a reporter gens, such as chloramphenicol acetyl transferass or luciferass, and then transfected into various cell types using the method described herein. Expression of the reporter gens determines the tissue specificity of the regulatory sequence.

---

What is claimed is:

1. A transfection vector comprising a synthetic polypeptide linked electrostatically to a DNA structural sequence, forming a polypeptide-DNA complex, wherein said polypeptide is comprised of (A) a polymeric chain of basic amino acid residues, (B) a nuclear localization signal (NLS) peptide and (C) a hinge region of neutral amino acids that connects said polymeric chain and said NLS peptide.

2. The vector of claim 1, wherein said polymeric chain is comprised of between 10 and 50 residues.

3. The vector of claim 1, wherein said basic amino acid residues are selected from the group consisting of lysine, arginine and ornithine.

4. The vector of claim 1, wherein said NLS peptide is selected from the group consisting of a Simian Virus 40 (SV40) large T antigen nuclear localization signal sequence, a polyoma large T antigen nuclear localization signal sequence, an adenovirus E1a nuclear localization signal sequence, and an adenovirus E1b nuclear localization signal sequence.

5. The vector of claim 1, wherein said hinge region is comprised of between 6 and 50 amino acid residues.

6. The vector of claim 1, wherein said neutral amino acids are selected from the group consisting of glycine, alanine, leucine and isoleucine.

7. The vector of claim 1, wherein said NLS peptide is located at the amino terminus of said polypeptide and said polymeric basic amino acid chain is located at the carboxyl terminus.

8. The transfection vector of claim 1, further comprising (D) a cell type-specific ligand molecule.

9. The transfection vector of claim 1, wherein said DNA structural sequence comprises (a) a segment coding for SV40 large T antigen or polyoma large T antigen and (b) a transcription factor gene.

10. A vector according to claim 1, wherein said DNA structural sequence comprises an oncogene.

11. A vector according to claim 10, wherein said oncogene is selected from the group consisting of SV40 large T antigen, polyoma large T antigen, adenovirus E1A, adenovirus E1B, v-fms, BC12, myc, and ras.

12. A vector according to claim 1, wherein said DNA structural sequence comprises a DNA sequence selected from the group consisting of a dihydrofolate reductase gens (DHFR), a thymidine kinase gens, a thymidylate synthetase gene a DRTF1/E2F transcription factor-encoding DNA sequence, and an E2F transcription factor-encoding DNA sequence.

13. A process for producing a transformed mammalian cell line, comprising the step of transfecting a mammalian cell with a vector according to claim 1, wherein said DNA structural sequence comprises a DNA sequence selected from the group consisting of a dihydrofolate reductase gene (DHFR), a thymidine kinase gene, a thymidylate synthetase gene a DRTF1/E2F transcription factor-encoding DNA sequence, and an E2F transcription factor-encoding DNA sequence.

14. A process for producing a transformed mammalian cell line, comprising the step of transfecting a mammalian cell with a vector according to claim 1, wherein said DNA structural sequence comprises an oncogene.

* * * * *

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Lys  Ile  Pro  Ile  Lys
    1                      5

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
        Val  Arg  Ile  Leu  Glu  Ser  Trp  Phe  Ala  Lys  Asn  Ile
        1              5                        10
```

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
        Pro  Lys  Lys  Lys  Arg  Lys  Val
        1              5
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
        Ala  Ala  Phe  Glu  Asp  Leu  Arg  Val  Arg  Ser
        1              5                        10
```

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
        Pro  Arg  Lys  Arg
        1
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
        Val  Ser  Arg  Lys  Arg  Pro  Arg  Pro  Ala
        1              5
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
        Ala  Pro  Thr  Lys  Arg  Lys
        1              5
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single ( D ) TOPOLOGY: linear ( x i ) SEQUENCE DESCRIPTION: SEQ ID NO:8:

Lys Arg Pro Arg Pro
1               5

( 2 ) INFORMATION FOR SEQ ID NO:9:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( x i ) SEQUENCE DESCRIPTION: SEQ ID NO:9:

Pro Met Lys Lys Lys Arg Lys
1               5

( 2 ) INFORMATION FOR SEQ ID NO:10:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( x i ) SEQUENCE DESCRIPTION: SEQ ID NO:10:

Arg Pro Ala Ala Thr Lys Lys Ala Gly Gln Ala Lys Lys Lys Lys Leu
1               5                   10                  15

Asp ( 2 ) INFORMATION FOR SEQ ID NO:11:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( x i ) SEQUENCE DESCRIPTION: SEQ ID NO:11:

Lys Lys Lys Ile Lys
1               5

( 2 ) INFORMATION FOR SEQ ID NO:12:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( x i ) SEQUENCE DESCRIPTION: SEQ ID NO:12:

Arg Val Thr Ile Arg Thr Val Arg Val Arg Arg Pro Pro Lys Gly Lys
1               5                   10                  15

His Arg Lys ( 2 ) INFORMATION FOR SEQ ID NO:13:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( x i ) SEQUENCE DESCRIPTION: SEQ ID NO:13:

Gly Lys Lys Arg Ser Lys Ala
1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:14:

```
Lys Ala Lys Arg Ser Lys Ala
1               5
```

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:15:

```
Asp Arg Leu Arg Arg
1               5
```

(2) INFORMATION FOR SEQ ID NO:16:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:16:

```
Pro Lys Gln Lys Arg Lys
1               5
```

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:17:

```
Val Arg Lys Lys Arg Lys Thr
1               5
```

(2) INFORMATION FOR SEQ ID NO:18:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:18:

```
Ala Lys Lys Ser Lys Gln Glu
1               5
```

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: single
        (D) TOPOLOGY: linear ( x i ) SEQUENCE DESCRIPTION: SEQ ID NO:19:

Pro Ala Ala Lys Arg Val Lys Leu Asp
1               5

( 2 ) INFORMATION FOR SEQ ID NO:20:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( x i ) SEQUENCE DESCRIPTION: SEQ ID NO:20:

Arg Gln Arg Arg Asn Glu Leu Lys Ser Phe
1               5                   10

( 2 ) INFORMATION FOR SEQ ID NO:21:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:21:

Thr Lys Lys Arg Lys Leu Glu
1               5

( 2 ) INFORMATION FOR SEQ ID NO:22:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:22:

Pro Lys Thr Arg Arg Arg Pro
1               5

( 2 ) INFORMATION FOR SEQ ID NO:23:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:23:

Ser Gln Arg Lys Arg Pro Pro
1               5

( 2 ) INFORMATION FOR SEQ ID NO:24:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( x i ) SEQUENCE DESCRIPTION: SEQ ID NO:24:

Arg Leu Pro Val Arg Arg Arg Arg Arg Val Pro
1               5                   10

( 2 ) INFORMATION FOR SEQ ID NO:25:

( i ) SEQUENCE CHARACTERISTICS:
    ( A ) LENGTH: 5 amino acids (B) TYPE: amino acid
(C) STRANDEDNESS: single
(D) TOPOLOGY: linear (xi) SEQUENCE DESCRIPTION: SEQ ID NO:25:

Gly Arg Lys Lys Arg
1               5

(2) INFORMATION FOR SEQ ID NO:26:

(i) SEQUENCE CHARACTERISTICS:
(A) LENGTH: 13 amino acids
(B) TYPE: amino acid
(C) STRANDEDNESS: single
(D) TOPOLOGY: linear (xi) SEQUENCE DESCRIPTION: SEQ ID NO:26:

Val Arg Thr Thr Lys Gly Lys Arg Lys Arg Ile Asp Val
1               5                   10

(2) INFORMATION FOR SEQ ID NO:27:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:27:

Arg Lys Phe Lys Lys
1               5

(2) INFORMATION FOR SEQ ID NO:28:

(i) SEQUENCE CHARACTERISTICS:
(A) LENGTH: 8 amino acids
(B) TYPE: amino acid
(C) STRANDEDNESS: single
(D) TOPOLOGY: linear (xi) SEQUENCE DESCRIPTION: SEQ ID NO:28:

Arg Arg Asn Arg Arg Arg Arg Trp
1               5

(2) INFORMATION FOR SEQ ID NO:29:

(i) SEQUENCE CHARACTERISTICS:
(A) LENGTH: 15 amino acids
(B) TYPE: amino acid
(C) STRANDEDNESS: single
(D) TOPOLOGY: linear (xi) SEQUENCE DESCRIPTION: SEQ ID NO:29:

Pro Arg Ser Gly Lys Lys Arg Lys Arg Lys Arg Leu Lys Pro Thr
1               5                   10                  15

(2) INFORMATION FOR SEQ ID NO:30:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:30:

Lys Lys Lys Lys Lys
1               5

( 2 ) INFORMATION FOR SEQ ID NO:31:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:31:

```
Pro  Pro  Lys  Lys  Arg
1                   5
```

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:32:

```
Pro  Lys  Lys  Lys  Lys  Lys
1                   5
```

( 2 ) INFORMATION FOR SEQ ID NO:33:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:33:

```
Ser  Lys  Arg  Val  Ala  Lys  Arg  Lys  Leu
1                   5
```

( 2 ) INFORMATION FOR SEQ ID NO:34:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:34:

```
Pro  Leu  Leu  Lys  Lys  Ile  Ile  Gln
1                   5
```

( 2 ) INFORMATION FOR SEQ ID NO:35:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:35:

```
Pro  Pro  Gln  Lys  Lys  Ile  Lys  Ser
1                   5
```

( 2 ) INFORMATION FOR SEQ ID NO:36:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:36:

```
   Pro  Gln  Pro  Lys  Lys  Lys  Pro
   1                 5
```

( 2 ) INFORMATION FOR SEQ ID NO:37:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( x i ) SEQUENCE DESCRIPTION: SEQ ID NO:37:

```
   Phe  Lys  Arg  Lys  His  Lys  Lys  Asp  Ile  Ser  Gln  Asn  Lys  Arg  Ala  Val
   1                 5                           10                          15
   Arg  Arg
```

( 2 ) INFORMATION FOR SEQ ID NO:38:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:38:

```
   Ser  Lys  Cys  Leu  Gly  Trp  Leu  Trp  Gly
   1                 5
```

( 2 ) INFORMATION FOR SEQ ID NO:39:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:39:

```
   Gly  Lys  Arg  Lys  Asn  Lys  Pro  Lys
   1                 5
```

( 2 ) INFORMATION FOR SEQ ID NO:40:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:40:

```
   Lys  Thr  Arg  Lys  His  Arg  Gly
   1                 5
```

( 2 ) INFORMATION FOR SEQ ID NO:41:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:41:

```
   Lys  His  Arg  Lys  His  Pro  Gly
   1                 5
```

( 2 ) INFORMATION FOR SEQ ID NO:42:

( i ) SEQUENCE CHARACTERISTICS:
        ( A ) LENGTH: 18 amino acids (B) TYPE: amino acid
(C) STRANDEDNESS: single
(D) TOPOLOGY: linear (xi) SEQUENCE DESCRIPTION: SEQ ID NO:42:

Arg Arg Leu Ala Gln Asn Arg Glu Ala Ala Arg Lys Ser Arg Leu Arg
1               5                   10                  15
Lys Lys (2) INFORMATION FOR SEQ ID NO:43:

(i) SEQUENCE CHARACTERISTICS:
(A) LENGTH: 16 amino acids
(B) TYPE: amino acid
(C) STRANDEDNESS: single
(D) TOPOLOGY: linear (xi) SEQUENCE DESCRIPTION: SEQ ID NO:43:

Lys Lys Arg Ala Arg Leu Val Arg Asn Arg Glu Ser Ala Gln Leu Ser
1               5                   10                  15

(2) INFORMATION FOR SEQ ID NO:44:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:44:

Arg Gln Arg Lys Lys
1               5

(2) INFORMATION FOR SEQ ID NO:45:

(i) SEQUENCE CHARACTERISTICS:
(A) LENGTH: 18 amino acids
(B) TYPE: amino acid
(C) STRANDEDNESS: single
(D) TOPOLOGY: linear (xi) SEQUENCE DESCRIPTION: SEQ ID NO:45:

Arg Lys Arg Lys Glu Ser Asn Arg Glu Ser Ala Arg Arg Ser Arg Tyr
1               5                   10                  15
Arg Lys (2) INFORMATION FOR SEQ ID NO:46:

(i) SEQUENCE CHARACTERISTICS:
(A) LENGTH: 13 amino acids
(B) TYPE: amino acid
(C) STRANDEDNESS: single
(D) TOPOLOGY: linear (xi) SEQUENCE DESCRIPTION: SEQ ID NO:46:

Lys Lys Asn Gln Lys His Lys Leu Lys Met Lys Arg Lys
1               5                   10

(2) INFORMATION FOR SEQ ID NO:47:

(i) SEQUENCE CHARACTERISTICS:
(A) LENGTH: 18 amino acids
(B) TYPE: amino acid
(C) STRANDEDNESS: single
(D) TOPOLOGY: linear (xi) SEQUENCE DESCRIPTION: SEQ ID NO:47:

```
Lys  Arg  Pro  Arg  Glu  Asp  Asp  Asp  Gly  Glu  Pro  Ser  Glu  Arg  Lys  Arg
 1             5                        10                       15
Glu  Arg
```

( 2 ) INFORMATION FOR SEQ ID NO:48:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:48:

```
Lys  Leu  Arg  Pro  Glu  Asp  Arg  Tyr  Ile  Gln  Thr  Glu  Lys  Tyr  Gly  Arg
 1             5                        10                       15
Arg
```

( 2 ) INFORMATION FOR SEQ ID NO:49:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:49:

```
Lys  Thr  Lys  Tyr  Gly  Ser  Asp  Thr  Glu  Ile  Lys  Leu  Leu  Ser  Lys
 1             5                        10                       15
```

( 2 ) INFORMATION FOR SEQ ID NO:50:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO:50:

```
Met  Glu  Glu  Ala  Val  Thr  Met  Ala  Pro  Ala  Ala  Val  Ser  Ser  Ala  Val
 1             5                        10                       15
Val  Gly  Asp  Pro
                20
```

( 2 ) INFORMATION FOR SEQ ID NO:51:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:51:

```
Met  Tyr  Asn  Ala  Ile  Leu  Arg  Arg  Lys  Leu  Glu  Glu  Asp  Leu  Glu
 1             5                        10                       15
```

( 2 ) INFORMATION FOR SEQ ID NO:52:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:52:

```
Gly  Asp  Arg  Arg  Ala  Ala  Pro  Ala  Arg  Pro
 1             5                        10
```

(2) INFORMATION FOR SEQ ID NO:53:

(i) SEQUENCE CHARACTERISTICS:
     (A) LENGTH: 10 amino acids
     (B) TYPE: amino acid
     (C) STRANDEDNESS: single
     (D) TOPOLOGY: linear (xi) SEQUENCE DESCRIPTION: SEQ ID NO:53:

```
Met  Ser  Glu  Arg  Lys  Arg  Arg  Glu  Lys  Leu
 1              5                        10
```

(2) INFORMATION FOR SEQ ID NO:54:

(i) SEQUENCE CHARACTERISTICS:
     (A) LENGTH: 13 amino acids
     (B) TYPE: amino acid
     (C) STRANDEDNESS: single
     (D) TOPOLOGY: linear (xi) SEQUENCE DESCRIPTION: SEQ ID NO:54:

```
Met  Ile  Ser  Glu  Ala  Leu  Arg  Lys  Ala  Ile  Gly  Lys  Arg
 1              5                        10
```

(2) INFORMATION FOR SEQ ID NO:55:

(i) SEQUENCE CHARACTERISTICS:
     (A) LENGTH: 16 amino acids
     (B) TYPE: amino acid
     (C) STRANDEDNESS: single
     (D) TOPOLOGY: linear (xi) SEQUENCE DESCRIPTION: SEQ ID NO:55:

```
Lys  Arg  Pro  Ala  Ala  Thr  Lys  Lys  Ala  Gly  Gln  Ala  Lys  Lys  Lys  Lys
 1              5                        10                       15
```

(2) INFORMATION FOR SEQ ID NO:56:

(i) SEQUENCE CHARACTERISTICS:
     (A) LENGTH: 25 amino acids
     (B) TYPE: amino acid
     (C) STRANDEDNESS: single
     (D) TOPOLOGY: linear (xi) SEQUENCE DESCRIPTION: SEQ ID NO:56:

```
Pro  Lys  Lys  Lys  Arg  Lys  Val  Ser  Gly  Gly  Gly  Gly  Gly  Lys  Lys  Lys
 1              5                        10                       15
Lys  Lys  Lys  Lys  Lys  Lys  Lys  Lys  Lys
             20                        25
```